(12) United States Patent
Seymour et al.

(10) Patent No.: US 9,259,567 B2
(45) Date of Patent: Feb. 16, 2016

(54) METHOD FOR MANUFACTURING AN IMPLANTABLE ELECTRONIC DEVICE

(71) Applicant: THE REGENTS OF THE UNIVERSITY OF MICHIGAN, Ann Arbor, MI (US)

(72) Inventors: John Seymour, Ann Arbor, MI (US); Mayurachat Ning Gulari, Ann Arbor, MI (US); Joerg Lahann, Ann Arbor, MI (US); Daryl Kipke, Dexter, MI (US)

(73) Assignee: The Regents Of The University Of Michigan, Ann Arbor, MI (US)

(*) Notice: Subject to any disclaimer, the term of this patent is extended or adjusted under 35 U.S.C. 154(b) by 91 days.

(21) Appl. No.: 14/051,886

(22) Filed: Oct. 11, 2013

(65) Prior Publication Data
US 2014/0039589 A1 Feb. 6, 2014

Related U.S. Application Data

(63) Continuation of application No. 12/619,224, filed on Nov. 16, 2009, now Pat. No. 8,561,292.

(60) Provisional application No. 61/114,630, filed on Nov. 14, 2008.

(51) Int. Cl.
*A61N 1/00* (2006.01)
*A61N 1/05* (2006.01)
*H01L 23/29* (2006.01)
*A61N 1/375* (2006.01)

(52) U.S. Cl.
CPC ............ *A61N 1/05* (2013.01); *H01L 23/293* (2013.01); *A61N 1/0551* (2013.01); *A61N 1/375* (2013.01); *H01L 2924/0002* (2013.01); *H01L 2924/3011* (2013.01); *Y10T 29/49117* (2015.01); *Y10T 29/49156* (2015.01)

(58) Field of Classification Search
CPC .................................. A61N 1/05; A61N 1/04
USPC ........................... 607/116; 600/378, 393, 372
See application file for complete search history.

(56) References Cited

U.S. PATENT DOCUMENTS

| 5,524,338 | A | 6/1996 | Martyniuk et al. |
| 2003/0100823 | A1* | 5/2003 | Kipke et al. ................ 600/378 |

(Continued)

FOREIGN PATENT DOCUMENTS

| WO | 2007089738 A2 | 8/2007 |
| WO | 2008011721 A1 | 1/2008 |

OTHER PUBLICATIONS

International Search Report and Written Opinion PCT/2009/064591 dated Jul. 21, 2010.

*Primary Examiner* — Christopher D Koharski
*Assistant Examiner* — Roland Dinga
(74) *Attorney, Agent, or Firm* — Harness, Dickey & Pierce, PLC

(57) ABSTRACT

A method of manufacturing an implantable electronic device, including: providing a silicon wafer; building a plurality of layers coupled to the wafer including an oxide layer coupled to the silicon wafer; a first reactive parylene layer coupled to the oxide layer, an electrode layer coupled to the first reactive parylene layer, and a second reactive parylene layer, coupled to the electrode layer, that chemically bonds to the first reactive polymer layer, and a second polymer layer coupled to the second reactive parylene layer; coating the plurality of layers with an encapsulation, and modifying the encapsulation and at least one of the plurality of layers to expose an electrode site in the electrode layer.

9 Claims, 5 Drawing Sheets

(56) References Cited

U.S. PATENT DOCUMENTS

| | | | |
|---|---|---|---|
| 2004/0087126 A1* | 5/2004 | Fartash | 438/597 |
| 2006/0282014 A1 | 12/2006 | Kipke et al. | |
| 2008/0255439 A1 | 10/2008 | Tang et al. | |
| 2009/0299167 A1* | 12/2009 | Seymour | 600/393 |

* cited by examiner

METHOD FOR MANUFACTURING AN IMPLANTABLE ELECTRONIC DEVICE

CROSS-REFERENCE TO RELATED APPLICATIONS

This application is a continuation of U.S. patent application Ser. No. 12/619,224 filed on 16 Nov. 2009, which claims the benefit of U.S. Provisional Application No. 61/114,630, filed 14 Nov. 2008, which are incorporated in their entirety by this reference.

This application is also related to prior applications US Patent Publication number 2007/0281126, filed 1 Jun. 2007, and International Patent PCT Publication WO 2007/089738, filed 26 Jan. 2007, which are each incorporated in its entirety by this reference.

GOVERNMENT INTEREST

This invention was made with government support under EB002030 awarded by the National Institutes of Health. The government has certain rights in the invention.

TECHNICAL FIELD

This invention relates generally to the implantable electronics field, and more specifically to an improved method for manufacturing an implantable electronic device.

BACKGROUND

Implantable microelectrode arrays are useful tools in various applications, including providing brain stimulation in the treatment of neurological and psychiatric disorders, as well as providing neuroscientists with the ability to research neurophysiology. Long-term use of implantable microelectrode arrays would expand these applications. However, conventional implantable microelectrodes have limited useful lifetimes when implanted in body tissue, because tissue encapsulation forms around the electrode site as a foreign body response, which often increases noise and electrical impedance between the electrode and tissue and decreases signal amplitude. Long-term use of implantable microelectrodes in the brain requires low electrical noise and high mechanical stability. Furthermore, interfacial boundary layers that form between each material in an implanted microelectrode should be clean, have similar surface energies, and possess adequate adhesion strength to withstand water, oxygen, ions, and other aspects of the surrounding environment. Polymers are an attractive choice of material because of their diverse bulk properties and alterable surface chemistry, but are inherently porous to water, oxygen, and salts, which decreases the long-term usefulness of a polymer implantable microelectrode. Thus, there is a need in the implantable electronics field to create an improved method to manufacture implantable electronics. This invention provides such an improved method for manufacturing an implantable electronic device.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method for Manufacturing an Implantable Electronic Device

Figure 1:
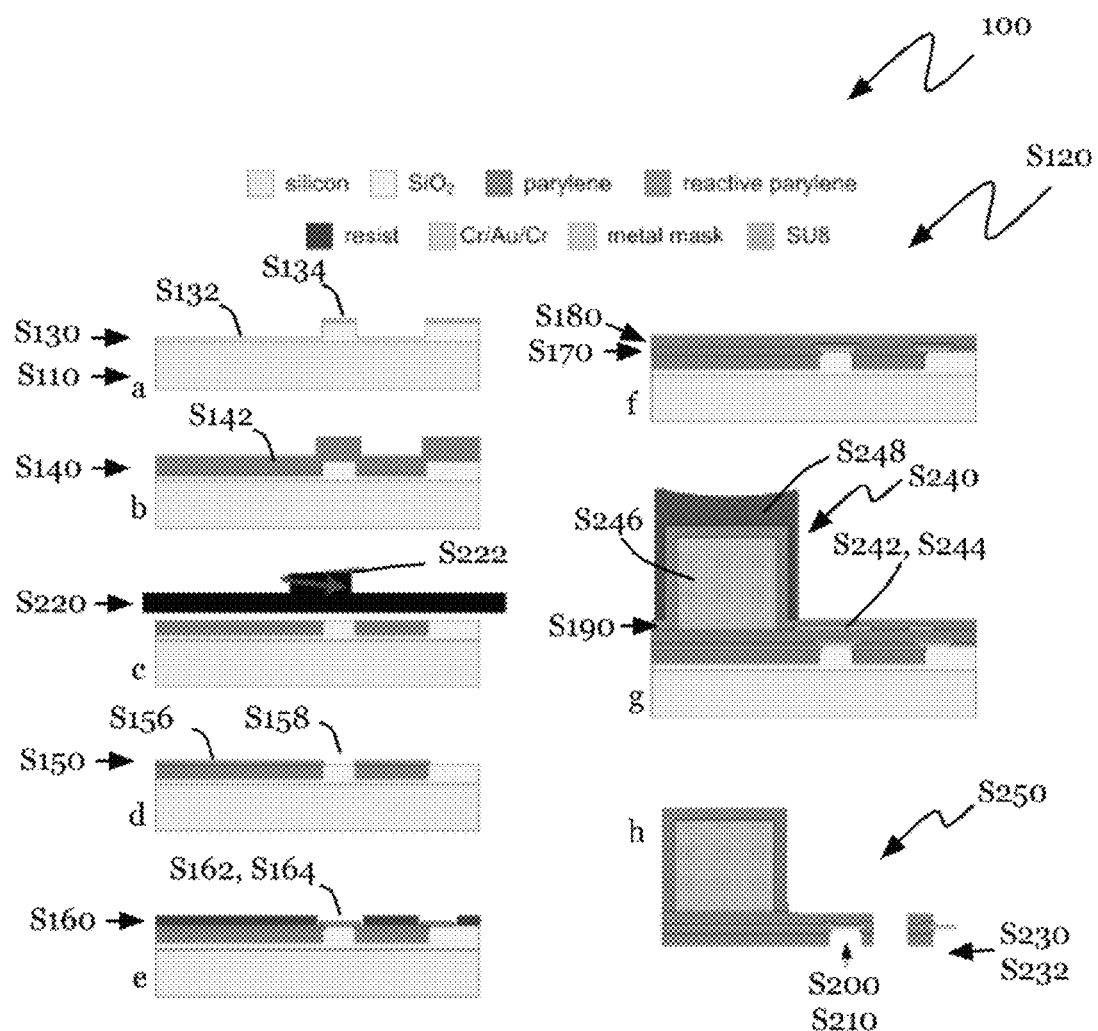
FIGS. 1A-1H is a schematic of the steps of the method of the preferred embodiment.
Figure 3:
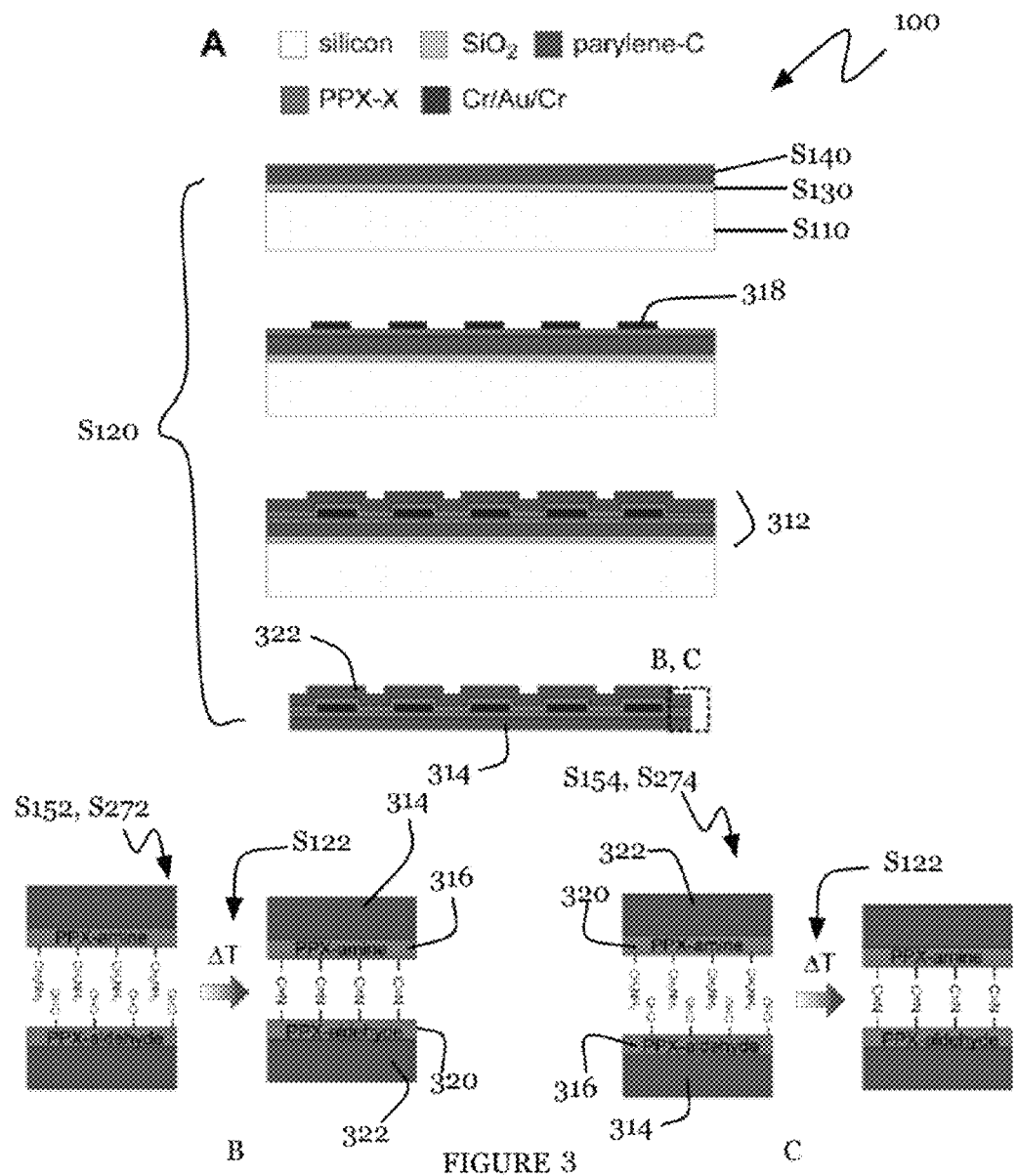
FIG. 3A is a schematic of the steps of the method of the preferred embodiment.
FIGS. 3B and 3C are detailed views of variations of the steps of building reactive polymer layers in the method of the preferred embodiment.

As shown in FIGS. 1 and 3, the method 100 for manufacturing an implantable electronic device of the preferred embodiments preferably includes the steps of: providing a silicon wafer S110; building a plurality of layers coupled to the wafer S120, including building an oxide layer coupled to the wafer S130, building a first polymer layer coupled to the oxide layer S140, building a first reactive parylene layer coupled to the first polymer layer S150, building an electrode layer coupled to the first reactive parylene layer S160, building a second reactive parylene layer coupled to the electrode layer S170, and building a second polymer layer coupled to the second reactive parylene layer S180; coating the plurality of layers with an encapsulation S190; and modifying the encapsulation and at least one of the plurality of layers to expose an electrode site in the electrode layer S200. The method is preferably used to manufacture implantable electrodes and more preferably an implantable neural electrode array, such as a three-sided electrode probe (FIG. 5A), an interdigitated electrode probe (FIG. 5B), an open channel electrode probe with a drug delivery well for passive drug delivery (FIG. 5C) or a hollow channel probe with a cell-delivery well for cell-based therapies (exemplified in FIG. 5D). Alternatively, the method can be used to manufacture an implantable biosensor, a smart drug delivery system, a neuroprosthesis, or any suitable implantable electronic device. The method preferably provides the implantable electronic device with improved interfacial layer adherence and improved insulation performance for an overall improved implantable electronic device performance.

The step of providing a silicon wafer S110 functions to provide a substrate on which to develop the electronic device. The silicon wafer is preferably a wafer substrate made of silicon, but may alternatively be any substrate useable in manufacturing of semiconductors or integrated circuits, or any suitable material.

The step of building a plurality of layers on the wafer S120 functions to create a stack of conductive and insulating materials that comprise and may be modified to form the implantable electronic device. The step of building a plurality of layers on the wafer S120 preferably includes the steps of building an oxide layer onto the wafer S130, building a first polymer layer onto the oxide layer S140, building a first reactive parylene layer onto the first polymer layer S150, building an electrode layer onto the first reactive parylene layer S160, building a second reactive parylene layer onto the electrode layer S170, and building a second polymer layer onto the second reactive parylene layer S180. The step of building a plurality of layers may further include etching at least one of the plurality of layers to define an electrode location and etching at least one of the plurality of layers to define an electrode opening aligned with the electrode location.

The step of building an oxide layer S130 functions to provide a sacrificial release layer and form electrode and/or bond pad location placeholders. Building an oxide layer S130 preferably includes applying an oxide layer to the wafer S132 and patterning the oxide layer to define an electrode location S134. Applying an oxide layer to the wafer S132 is preferably performed by vapor deposition, but may alternatively be performed through any suitable process. Patterning the oxide layer to define an electrode location S134 is preferably performed by patterning an aluminum mask using standard lithography processes common in making integrated circuits and a wet etchant or other suitable etchant or process, then patterning the oxide layer with the patterned aluminum mask and an etchant. The oxide layer is preferably patterned using a dry etch, and more preferably with a dry hexafluoroethane ($C_2F_6$) etchant. However, the oxide layer may alternatively be patterned with any suitable material mask and/or any suitable dry etchant, wet etchant, or any suitable process. The oxide layer is preferably patterned to a depth of approximately 2.8 μm and patterned such as to define a planar electrode location for one or more electrode sites and/or bond pads, but may alternatively be patterned with any suitable size and/or geometry. The oxide layer is preferably high-temperature silicon dioxide heated to approximately 910 degrees Celsius, but may alternatively be any suitable temperature, and any suitable oxide or other material. After the oxide layer is patterned, the aluminum mask is preferably removed and the wafer is preferably cleaned, such as by rinsing in a cleaning or a buffer solution. In some embodiments, the step of building an oxide layer may further include applying an adhesion promoter such as A-174 to the wafer. The adhesion promoter may be applied to the wafer through dip coating, vapor deposition, spin coating or any suitable process.

The step of building a first polymer layer S140 functions to provide a barrier film layer that helps to electrically insulate the electrode layer. The step of building a first polymer layer S140 preferably includes applying the first polymer layer to the oxide layer S142. Applying the first polymer layer is preferably performed through chemical vapor deposition (CVD), which polymerizes the first polymer layer on the oxide. Applying the first polymer layer to the oxide layer may alternatively be performed through physical vapor deposition (PVD), any semiconductor manufacturing process, or any suitable process. The first polymer layer is preferably approximately 4 μm thick, but may be any suitable thickness. The first polymer layer is preferably parylene, and more preferably parylene-C, but may alternatively be any suitable material.

The steps of building a first reactive parylene layer S150 and building a second reactive parylene layer S170 function to provide a stable interfacial boundary on both sides of the electrode layer to help electrically insulate the electrode layer. The first reactive parylene layer and the second reactive parylene layer preferably adhere well to the electrode layer. Furthermore, the first reactive parylene layer and the second reactive parylene layer are preferably chemically complementary to each other, such that they chemically bond and adhere well to each other. The adherence of the reactive parylene layers to the electrode layer and to each other preferably reduces impedance and improve overall electrode performance. The step of building a first reactive parylene layer S150 preferably includes applying the first reactive parylene layer to the first polymer layer S156 and creating an electrode opening aligned with the electrode location defined by the oxide layer S158. Applying the first reactive parylene layer to the first polymer layer is preferably performed through CVD, but may alternatively be performed through any suitable process. The first reactive parylene layer is preferably approximately 80-130 nanometers thick, and more preferably approximately too nanometers thick, but may alternatively be any suitable thickness. In some variations, the step of building a first reactive parylene layer may further include performing a plasma cleaning on the first polymer layer prior to applying the first reactive parylene layer, which functions to clean the first polymer layer and enhance adhesion of the first reactive parylene layer to the first polymer layer. In some variations, the plasma cleaning step may be performed before each step performed with a CVD process. The step of creating an electrode opening aligned with the electrode location S158 preferably includes etching an electrode opening in the first reactive polymer, and more preferably with a photoresist mask and an oxygen plasma etch. However, creating an electrode opening may alternatively be performed through any suitable process.

The step of building a second reactive parylene layer S170 is preferably similar to the step of building a first reactive parylene layer, except that the second reactive parylene layer is applied to the electrode layer and may include performing a plasma cleaning on the first reactive parylene layer and/or the electrode layer prior to applying the second reactive parylene layer.

The first reactive parylene layer and second reactive parylene layer may be one of several variations. In a first variation, as shown in FIG. 3B, building a first reactive parylene layer includes building a first reactive parylene (poly (p-xylylene), or PPX) layer having parylene functionalized with an aminomethyl group S152, and building a second reactive parylene layer includes building a second reactive parylene layer having parylene functionalized with an aldehyde group S272. In this variation, the step of building a plurality of layers preferably includes the step of heat-treating the first reactive parylene layer and the second reactive parylene layer S122, such that the aminomethyl and aldehyde groups of the first and second reactive parylene layers, respectively, covalently react to form an imine linkage after heating. The heat-treated first and second reactive parylene layers preferably have improved adherence strength and provide improved electrical insulation for the electrode layer as a result of the imine linkage. The first and second reactive parylene layers are preferably heated to approximately 140 degrees Celsius for approximately 3 hours, but may alternatively be heated to any suitable temperature for any suitable amount of time. Alternatively, the first and second reactive parylene layers are not heat-treated, but still have substantial adherence strength and electrical insulation. A Fourier transform infrared spectroscopy spectrum may be used to confirm the presence of the aminomethyl group after deposition of the first reactive parylene (preferably peaks at 3361 $cm^{-1}$ and 3301 $cm^{-1}$ in the infrared spectrum) and the presence of the aldehyde group after deposition of the second reactive parylene (preferably peaks at 1688 $cm^{-1}$ in the IR spectrum).

In a second variation, as shown in FIG. 3C, building a first reactive parylene layer includes building a first reactive parylene layer having parylene functionalized with an aldehyde group S154, and building a second reactive parylene layer includes building a second reactive parylene layer having parylene functionalized with an aminomethyl group S274. The second variation of the first and second reactive parylene layers is preferably similar to the first variation, except that the first reactive parylene layer preferably is a reactive parylene film layer having parylene functionalized with an aldehyde group and the second reactive parylene layer is a reactive parylene film layer having parylene functionalized with an aminomethyl group.

In a third variation of the method, the step of building a plurality of layers S120 includes building a first heat-treated parylene layer coupled to the first polymer layer and building a second heat-treated parylene layer coupled to the electrode layer. The first and second heat-treated parylene layers are preferably heat-treated similarly to the heat-treated first and second reactive parylene layers of the first variation.

The step of building an electrode layer S160 functions to provide a conductive layer that provides electrode sites, bond pads, and/or interconnects that transfer signals between the electrode sites and bond pads for electrical connections. The electrode sites may be used for stimulation and/or recording. The step of building an electrode layer preferably includes building a series of layers S164 including a gold layer sandwiched between two chromium layers and building an electrode site S162. The top and bottom chromium layers are each preferably approximately 100 angstroms thick, and the gold layer is preferably approximately 4000 angstroms thick, but the series of layers may alternatively be any suitable thicknesses. As shown in FIG. 1, the series of layers is preferably patterned and applied to the first reactive parylene layer through a metal lift-off process, but may alternatively be applied through vapor deposition or any suitable process. The electrode site is preferably a portion of the series of layers that is patterned such that the series of layers is applied in alignment with the electrode location and the electrode opening. The step of building an electrode layer may alternatively include building a series of layers including any suitable conductive material such as iridium or platinum, or any suitable material and/or pattern. The electrode sites may further include bond pads that provide a point of contact to an external connector.

The step of building a second polymer layer S180 is preferably similar to the step of building a first polymer layer S140, except that the second polymer layer couples to the second reactive parylene layer and is preferably 2.5 µm thick, but may be any suitable thickness.

The step of coating the plurality of layers with an encapsulation S190 functions to provide a highly biocompatible, barrier film to the device. The coating material is preferably parylene, and more preferably parylene-C, but may alternatively be any suitable polymer or other material. The coating is preferably a conformal coating that is applied to the plurality of layers through a CVD polymerization process, but may be applied through any suitable process.

Figure 4:
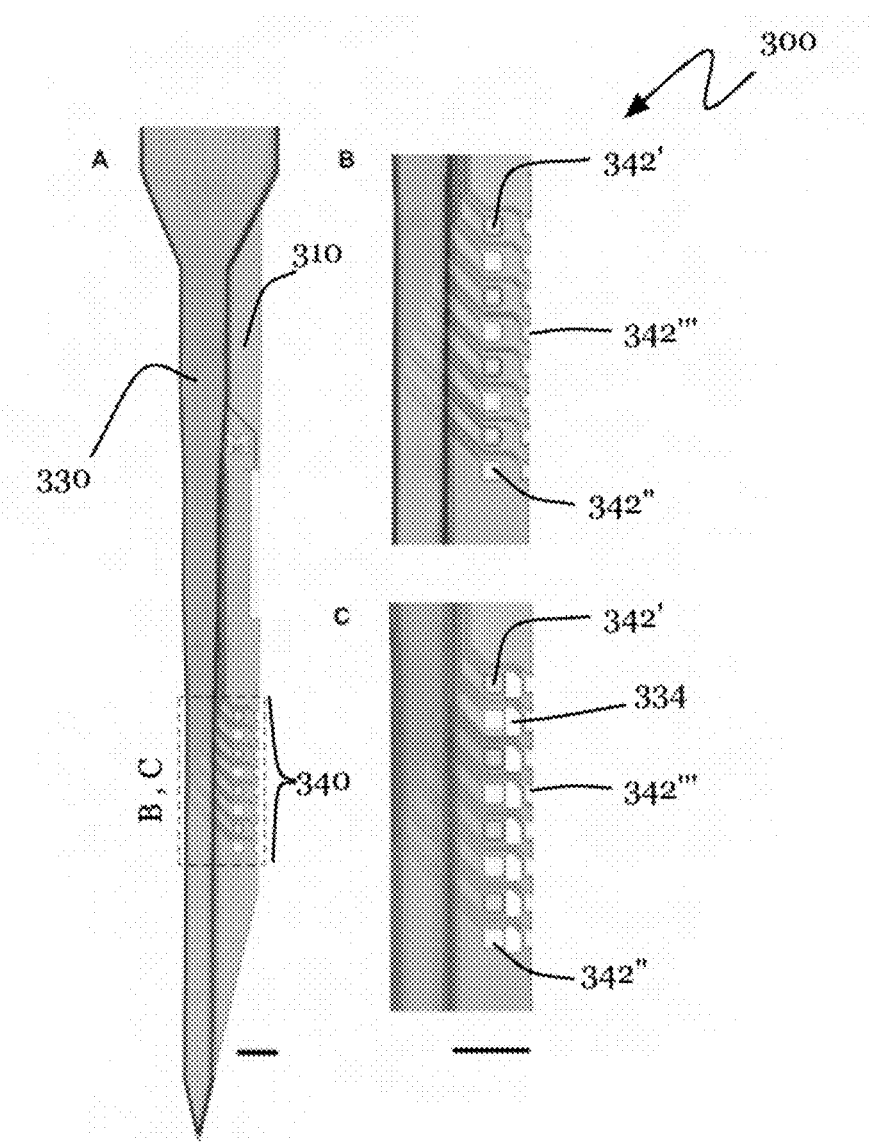
FIG. 4A is a schematic of an example implantable probe manufactured by the method of the preferred embodiment.
FIGS. 4B and 4C are detailed views of a solid platform variation and an open lattice platform variation, respectively, of the area taken in the dashed box in FIG. 4A.
Figure 5:
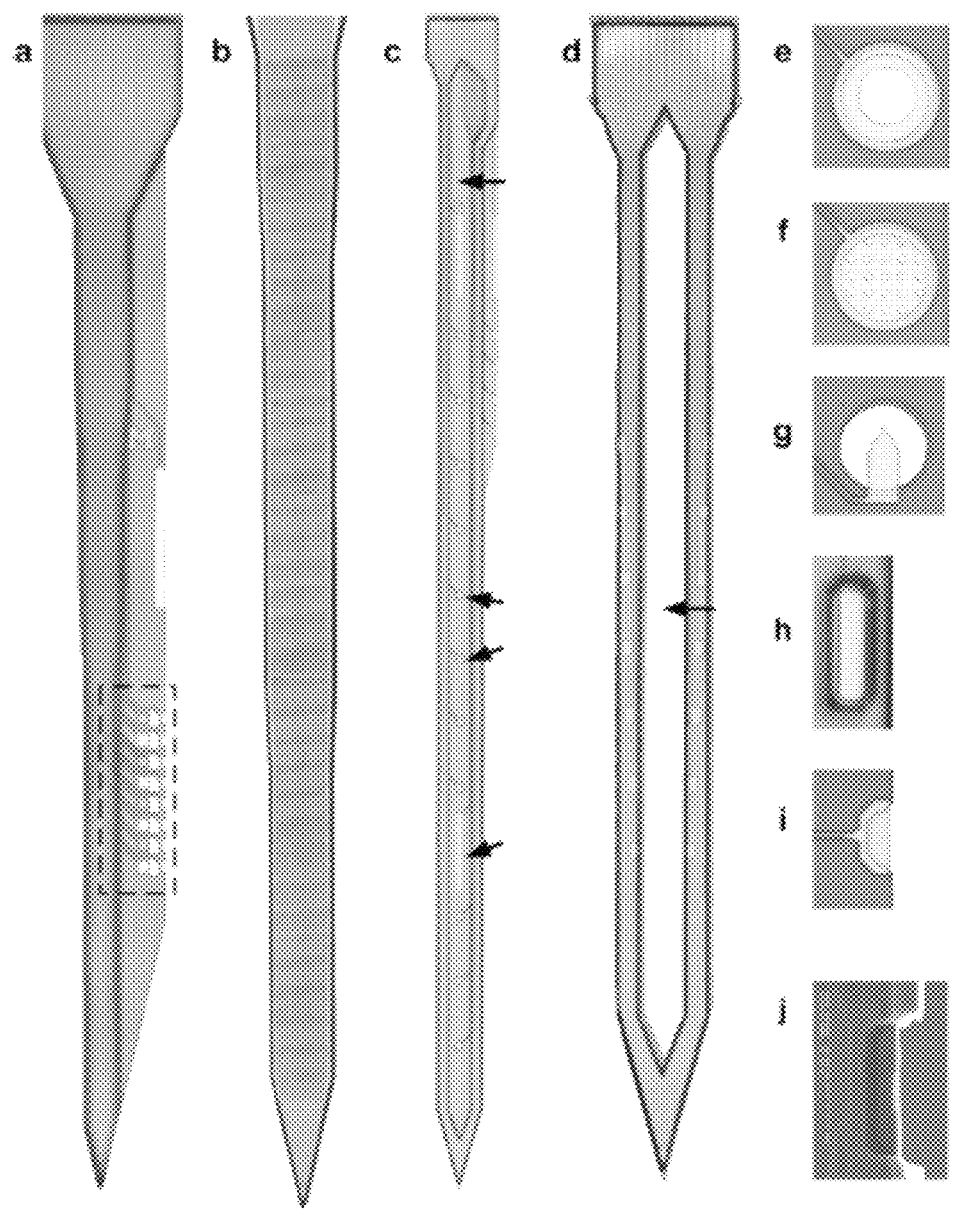
FIGS. 5A-5J are examples of implantable electronic devices that may be manufactured by the method of the preferred embodiment.

The step of modifying the encapsulation and at least one of the plurality of layers to expose an electrode site in the electrode layer S200 functions to expose an electrode site and/or bond pad to external electrical communication. Modifying the encapsulation and at least one of the plurality of layers S200 preferably includes removing a portion of at least one of the plurality of layers to expose a portion of the electrode layer S210. A portion of the chromium layer of the electrode layer is preferably removed to expose a portion of the gold layer of the electrode layer through a wet etching process, but alternatively any suitable portion of any suitable layer may be removed in any suitable process to expose an electrode site and/or bond pad. As shown in FIGS. 4 and 5, the electrode site may be one of several variations: planar rectangular (FIGS. 4 and 5A), ring (FIG. 5E), sieve (FIG. 5F), cantilever (FIG. 5G), reservoir (FIG. 5H), and edge (FIGS. 4, 5I and 5J).

The method may further include the step of planarizing at least one of the plurality of layers S220, which functions to polish at least one of the plurality of layers as flat and uniform as possible. Uniformity of insulation thickness and equal insulation thickness on each side of the electrode layer preferably controls internal stress of the electrode sites, bond pads, interconnects, and other features of the electrode layer, and results in uniform shunt capacitance and improved device performance. As shown in FIG. 1, the step of planarizing preferably includes planarizing the first polymer layer over the oxide layer. Planarization of the first polymer layer preferably results in a uniform insulation thickness, an equal insulation thickness on each side of the electrode layer, and/or a planar surface upon which the interconnect and electrode metal may be deposited. The step of planarizing preferably includes planarizing the first polymer layer and the oxide layer with a chemical mechanical polishing S222. The chemical mechanical polishing step is preferably performed with a potassium hydroxide-silica slurry mixture having a 0.2 µm silica size, pH of 10, and 10% solid load, but may alternatively have a slurry mixture of any suitable type. The chemical mechanical polishing is preferably performed in short polish intervals, each interval lasting less than approximately 4 minutes and the intervals interspersed with dehydration baking (such as at 90 degrees Celsius for 10 minutes, or any suitable temperature and length of time) to reduce likelihood of film delamination during the polishing step. Alternatively, the step of planarizing may include any suitable kind of planarization process.

The method may further include the steps of uncoupling the silicon wafer from the plurality of layers S230, uncoupling the oxide layer from the plurality of layers S232, filtering the device, and/or rinsing the device. The steps of uncoupling the silicon wafer S230 and uncoupling the oxide layer S232 preferably includes soaking the device in buffered hydrofluoric acid for at least three hours, but the device may alternatively be soaked in any suitable solution and/or amount of time. Alternatively, the steps of uncoupling the silicon wafer and uncoupling the oxide layer may include be performed through any suitable process. Rinsing the device preferably includes rinsing the device in deionized water, ethanol, acetone, and/or any suitable fluid.

The method may further include the step of electropolymerizing the electrode site, which functions to lower the electrical impedance of the electrode site. Electropolymerizing the electrode site preferably uses a solution of poly(3, 4ethylenedioxythiophane (PEDOT) and anion polystyrene sulfonate (PSS) to modify the electrode site, but may alternatively use any suitable substance.

In a preferred embodiment, the method further includes building a probe shank on the plurality of layers S240. Building a probe shank preferably includes depositing a titanium layer coupled to the second polymer layer S242, patterning the titanium layer to form a first mask S244, spinning and patterning a first thick resist onto the titanium layer S246, curing the first thick resist, spinning and patterning a second thick resist onto the encapsulation to form a second mask S248, and etching features of an electrode device S250. The titanium layer, which forms a mask to etch features of an electrode device on the plurality of layers, is preferably deposited on the second polymer layer with a thickness of approximately 1000 angstroms and patterned with a lithography process. As shown in FIG. 4, an example of etch features on the plurality of layers is an open lattice structure, which may improve tissue integration and local diffusion properties, and has a lowered structural stiffness that may better redistribute strain and better respond to micromotion in the tissue, which may result in more stable implantable probe. The first thick resist is preferably SU8-2025 resist spun onto a lateral side of the wafer with a thickness of approximately 40 µm, and patterned with a lithography process to form a core of a probe shank. The first thick resist is preferably cured in a vacuum oven at 15 degrees Celsius for approximately 15 minutes. The second thick resist, which forms a mask to etch features of an electrode device on the probe shank, is preferably AZ-9260 resist spun onto the core of the probe shank with a thickness of approximately 80 µm. Etching features of an electrode device, including that on the plurality of layers and on the probe shank, is preferably performed through an oxygen plasma etch. However, the step of building a probe shank may alternatively include any suitable processes.

2. Example

Figure 2:
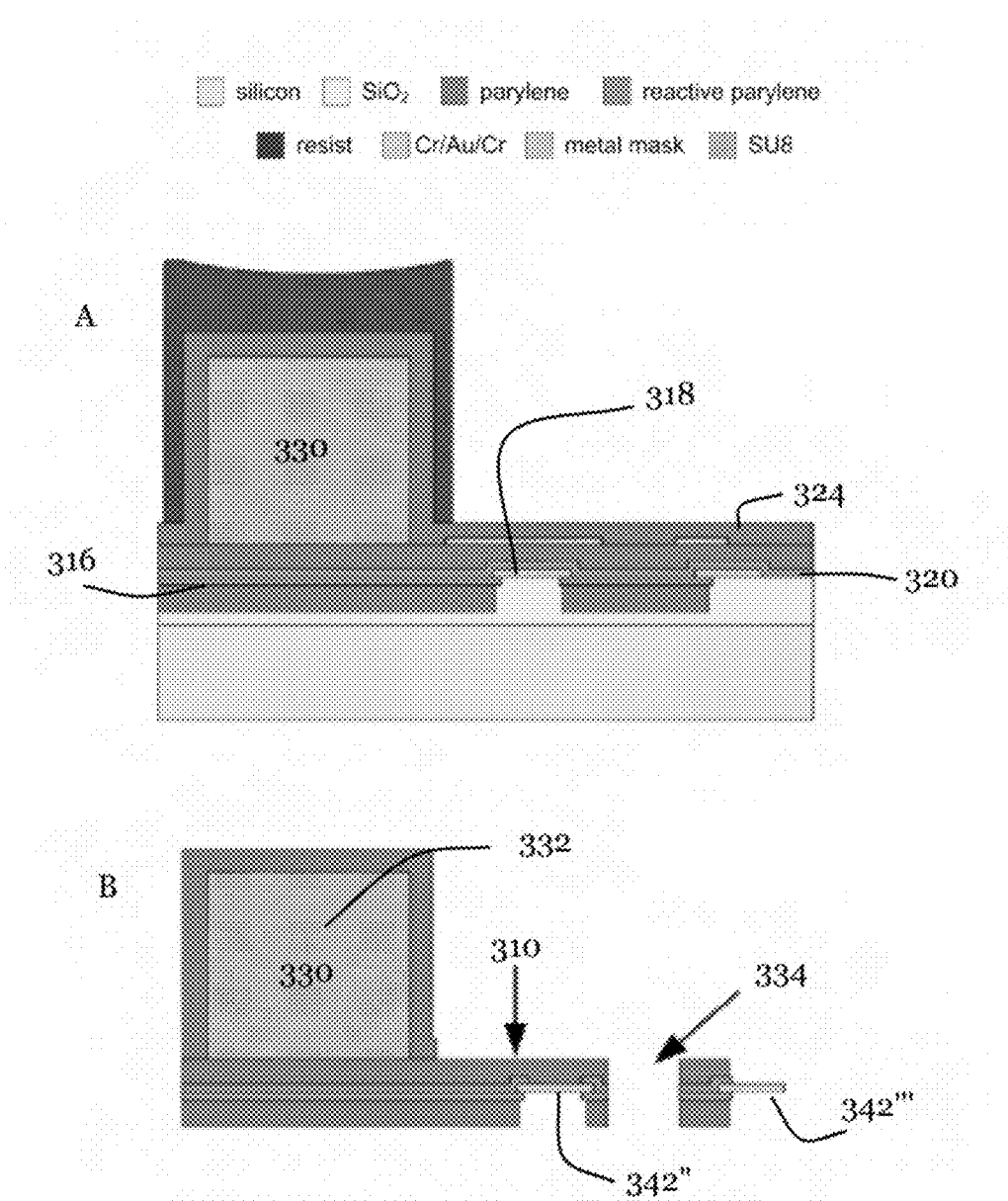
FIG. 2 is a schematic of a partially manufactured implantable electronic device manufactured with the steps of the method of the preferred embodiment.

As shown in FIGS. 2-4, one specific example of an implantable electronic device manufactured by the above described process is a sub-cellular edge electrode probe 300 that includes: a flexible platform 310 including a plurality of layers 312 and an electrode array 340 coupled to the flexible platform that includes a plurality of electrode sites 342, and a shank 330 coupled to a lateral side of the flexible platform that provides structural support for the flexible platform. The probe, intended for use with a rodent, is approximately 3 mm long and has 8 mm long interconnects.

The plurality of layers 312 of the flexible platform 310 includes a 4 µm thick parylene-C layer 314, a 100 nm thick reactive parylene layer 316 functionalized with an aminomethyl group, an electrode layer 318 including a 4000 angstrom thick gold layer sandwiched between two 100 angstrom thick chromium layers, a 100 nm thick reactive parylene layer 320 functionalized with an aldehyde group, and a 2.5 µm parylene-C layer 322. The electrode layer includes interconnects with a 2 µm track and 4 µm gap, and a uniform insulation thickness on each side of approximately 2.5 µm with a margin of 0.25 µm. The plurality of layers is further encapsulated with a conformal coating 324 of parylene-C. The first and second reactive parylene layers sandwich the electrode layer, and are heat treated at 140 degrees Celsius for 3 hours to initiate a covalent reaction forming an imide bond between the first and second reactive parylene layers. The platform is approximately 85 µm wide and 5 µm thick. As shown in FIG. 4B, in one embodiment, the platform is solid around the electrodes. As shown in FIG. 4C, in another embodiment, the platform includes an open lattice structure 334 around the electrodes formed through an oxygen plasma etching process using a patterned titanium mask.

The electrode array includes 16 sub-cellular sized electrode sites, including four top-side 17 µm×17 µm planar electrode sites 342' located on a top side of the flexible platform, four bottom-side 17 µm×17 µm planar electrode sites 342" located on a bottom side of the flexible platform, and eight 17 µm×7 µm edge electrode sites 342'" located on a lateral edge of the flexible platform. The electrode sites 342 are portions of the electrode layer that are exposed and accessible through openings in the other layers in the plurality of layers, such as the first and second reactive parylene layers.

The shank 330 includes a core of SU8-2020 thick resist cured at 150 degrees Celsius for 15 minutes and patterned through an oxygen plasma etching process using a patterned layer AZ-9260 thick film resist mask. The shank is approximately 70 µm wide and 45 µm thick and coupled to the flexible platform like a backbone, and includes a chisel tip that aids implantation of the probe into tissue.

As a person skilled in the art will recognize from the previous detailed description and from the figures and claims, modifications and changes can be made to the preferred embodiments of the invention without departing from the scope of this invention defined in the following claims.

We claim:

1. An implantable electronic device, comprising:
   a) a flexible platform having a top side, a bottom side, and a lateral edge and including a plurality of layers, wherein the plurality of layers includes a first parylene layer, and a second parylene layer chemically bonded to the first parylene layer, wherein the first parylene layer and the second parylene layer provide the flexible platform with a plurality of electrode openings; and
   b) an electrode array coupled to the flexible platform comprising a plurality of electrode sites, wherein the plurality of electrode sites includes planar electrode sites located on the top and bottom sides of the flexible platform and edge electrode sites located on the lateral edge of the flexible platform,
   c) wherein the plurality of electrode sites are aligned with the plurality of electrode openings in the first parylene layer and the second parylene layer.

2. The implantable electronic device of claim 1 wherein the first parylene layer includes parylene functionalized with an aminomethyl group and the second parylene layer includes parylene functionalized with an aldehyde group.

3. The implantable electronic device of claim 1 wherein the flexible platform includes an open lattice structure.

4. The implantable electronic device of claim 1 further comprising a chisel-shaped shank coupled to said lateral side of the flexible platform.

5. The implantable electronic device of claim 1 wherein at least one of the first and second parylene layers is a heat-treated reactive parylene layer.

6. The implantable electronic device of claim 1 wherein the first and second parylene layers are characterized as having been heated to at least 140° C.

7. The implantable electronic device of claim 1 wherein the plurality of electrode sites are substantially subcellular in size.

8. The implantable electronic device of claim 1 wherein the plurality of electrode sites each includes a chromium layer and a gold layer.

9. The implantable electronic device of claim 8 wherein the chromium layer is characterized as having been etched to expose a portion of the gold layer.

* * * * *